US012797074B2

(12) United States Patent
Binmoeller et al.

(10) Patent No.: US 12,797,074 B2
(45) Date of Patent: Nov. 17, 2026

(54) ENDOSCOPIC LOOP SYSTEMS AND METHODS OF USE

(71) Applicant: ENDOVISION FOUNDATION, San Francisco, CA (US)

(72) Inventors: Kenneth F. Binmoeller, San Francisco, CA (US); John P. Lunsford, San Carlos, CA (US); Hoang Phan, Milpitas, CA (US); Fiona Sander, Los Altos Hills, CA (US)

(73) Assignee: ENDOVISION FOUNDATION, San Francisco, CA (US)

( * ) Notice: Subject to any disclaimer, the term of this patent is extended or adjusted under 35 U.S.C. 154(b) by 212 days.

(21) Appl. No.: 18/580,329

(22) PCT Filed: Aug. 4, 2022

(86) PCT No.: PCT/US2022/039483
§ 371 (c)(1),
(2) Date: Jan. 18, 2024

(87) PCT Pub. No.: WO2023/014919
PCT Pub. Date: Feb. 9, 2023

(65) Prior Publication Data

US 2024/0307065 A1 Sep. 19, 2024

Related U.S. Application Data

(60) Provisional application No. 63/229,717, filed on Aug. 5, 2021.

(51) Int. Cl.
*A61B 17/12* (2006.01)

(52) U.S. Cl.
CPC .................. *A61B 17/12013* (2013.01); *A61B 2017/12004* (2013.01)

(58) Field of Classification Search
CPC .......... A61B 17/320056; A61B 17/221; A61B 17/12013; A61B 17/12009;
(Continued)

(56) References Cited

U.S. PATENT DOCUMENTS 5,782,840 A * 7/1998 Nakao .................... A61B 18/14 606/113
2001/0031970 A1* 10/2001 Heuser ............. A61B 17/32056 606/108

(Continued)

FOREIGN PATENT DOCUMENTS

JP 2016150044 A 8/2016

*Primary Examiner* — Katherine H Schwiker
(74) *Attorney, Agent, or Firm* — Christian S. Hans; Bret E. Field; Bozicevic, Field & Francis LLP

(57) ABSTRACT

The present embodiments provide apparatus and methods for treating tissue by applying a force to the tissue. In one embodiment, the apparatus comprises a deployable segment having a loop member formed at a distal region of the deployable segment. A frame is operatively coupled to the loop member. In some embodiments, the frame may be operatively coupled to the loop member by at least three lugs; each lug has a slit, and the loop member extends through each lug slit. The loop member includes a gauge diameter, the slit has an opening, and the slit opening may be narrower than the loop member gauge diameter.

35 Claims, 5 Drawing Sheets

(58) Field of Classification Search
CPC .. A61B 2017/2212; A61B 2017/12018; A61B 2018/1407; A61B 2018/141; A61B 2017/22031; A61B 2017/00358
See application file for complete search history.

(56) References Cited

U.S. PATENT DOCUMENTS

| | | | | |
|---|---|---|---|---|
| 2013/0144311 | A1 | 6/2013 | Fung et al. | |
| 2014/0276809 | A1 | 9/2014 | Smith et al. | |
| 2014/0378988 | A1 | 12/2014 | Raybin et al. | |
| 2016/0184009 | A1 | 6/2016 | Rosenblatt et al. | |
| 2016/0262763 | A1* | 9/2016 | Shankarsetty ... | A61B 17/12009 |
| 2016/0310155 | A1* | 10/2016 | Kimura .................. | A61B 17/29 |
| 2016/0324515 | A1* | 11/2016 | Ravikumar ........ | A61B 17/3468 |

* cited by examiner

ENDOSCOPIC LOOP SYSTEMS AND METHODS OF USE

CROSS-REFERENCE TO RELATED APPLICATIONS

This application claims the priority benefit of U.S. Provisional Patent Application Ser. No. 63/229,717, filed Aug. 5, 2021, the contents of which are herein incorporated by reference in their entirety.

TECHNICAL FIELD

This disclosure relates generally to medical devices, and more particularly, to apparatuses and methods for treating tissue by applying force by a loop member. Described herein are systems and methods for the deployment and engagement of endoscopic loop systems.

BACKGROUND

There are various instances in which it may become necessary or desirable to deliver a deployable snare into engagement with tissue. For example, such a snare may be used to induce hemostasis during a polypectomy, esophageal variceal bleeding, gastric variceal bleeding, or the excision of gastrointestinal stromal tumors. Further, deployable snares may be useful in ligation of varices or polyps, closure of gastrointestinal fistulas, and other procedures.

There are various commercially available deployable snares. Some deployable snares comprise a loop made of nylon, one or more elongated wires, sutures and/or other materials. The size and configuration of the loop may be adjusted using a stopper or cinching member that may be sized to surround first and second ends of the loop. As the stopper or cinching member is distally advanced relative to the loop, the size of the loop may be decreased, and a desired amount of force may be imposed upon target tissue. However, some commercially available applicators offer low control for placing a loop. The loops may deflect out of the intended plane of application and may be difficult to accurately control during placement.

SUMMARY

The present embodiments provide apparatus and methods for treating tissue by applying a force to the tissue.

In one embodiment, the apparatus comprises a deployable segment having a loop member formed at a distal region of the deployable segment. A frame is operatively coupled to the loop member. In any one of the preceding embodiments, the frame is coupled to at least three lugs. In any one of the preceding embodiments, each lug has a slit, and the loop member extends through each lug slit. The loop member includes a gauge diameter, the slit defines an opening, and the slit opening may be narrower than the loop member gauge diameter.

In any one of the preceding embodiments, the at least three lugs each include an aperture, and the frame extends through each lug aperture. In embodiments where the at least three lugs includes a first lug, a second lug, and a third lug, the first lug may be spaced apart from the second lug, and the second lug may be spaced apart from the third lug. Each of the at least three lugs further may comprise a first end and a second end, with a taper at the first end.

In any one of the preceding embodiments, the apparatus further includes a cannula with a lumen extending therethrough. The cannula is dimensioned to circumferentially surround at least a portion of the deployable segment and at least a portion of the frame.

In any one of the preceding embodiments, the frame has proximal and distal regions and a bend relative to a first longitudinal axis of the proximal region of the deployable segment. The distal region of the frame is collapsible, and the frame comprises a loop shape. The frame bend may be at an angle within a range of about 0 degrees to about 90 degrees. The frame bend is disposed proximal to the one or more lugs.

The present disclosure also provides methods of treating tissue by applying a force to the tissue. In one embodiment, a method includes expanding the frame, retracting the loop member, and deploying the deployable segment.

Other systems, methods, features, and advantages of the invention will be, or will become, apparent to one with skill in the art upon examination of the following figures and detailed description. It is intended that all such additional systems, methods, features, and advantages be within the scope of the invention and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Figure 1:
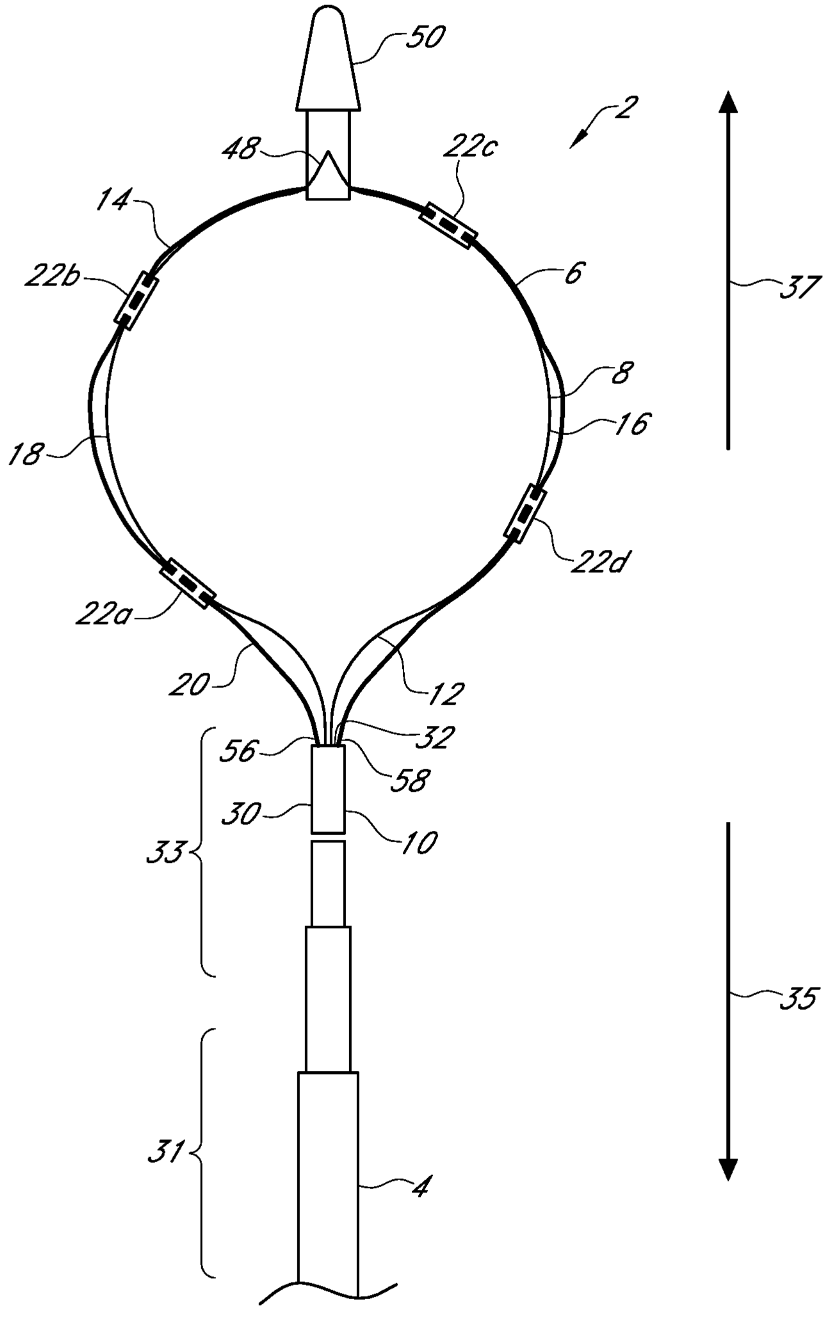
FIG. 1 is a front view of an embodiment of an apparatus including a frame and a loop member.

In the present application, the term “proximal” refers to a direction that is generally towards a physician during a medical procedure, while the term “distal” refers to a direction that is generally towards a target site within a patient’s anatomy during a medical procedure. Referring to FIG. 1, a first embodiment of a system 2 for treating tissue by applying a force to the tissue is shown. The system 2 has a proximal end 4 and distal end 6 and further includes a deployable segment 8 and a delivery segment 10. As will be described in greater detail herein, the deployable segment 8 may be disengaged from the delivery segment 10 and remain engaged with tissue. In some embodiments, the deployable segment 8 may remain engaged with tissue to provide a continuous compressive force upon the tissue.

Figure 7:
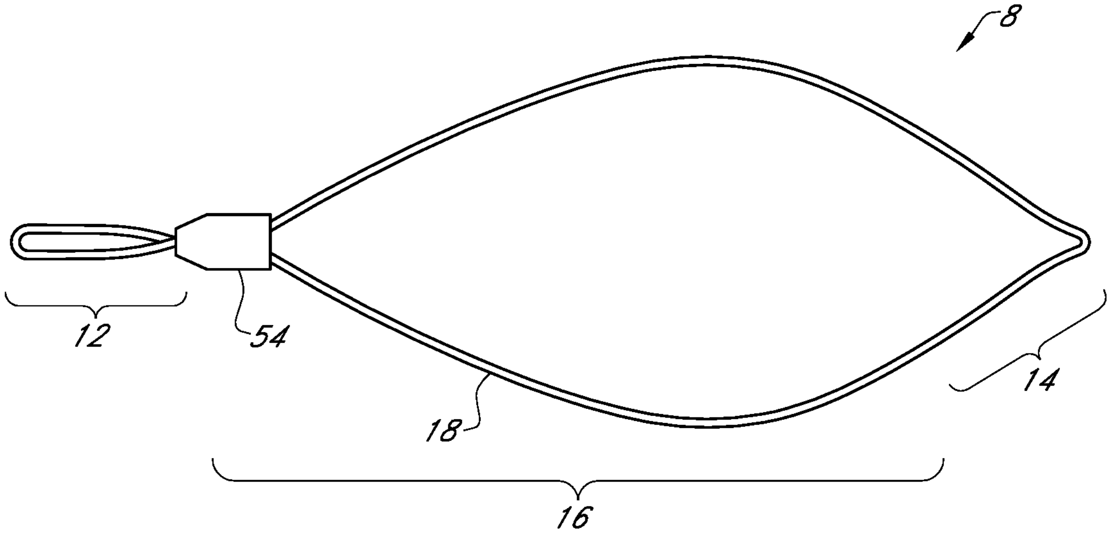
FIG. 7 is a side view of an embodiment of a deployable loop.

For illustrative purposes, one example of a deployable segment 8 is shown in FIG. 7 in an isolated manner, i.e., separate from delivery-related components. As can be seen in FIG. 7, the deployable segment 8 has a proximal region 12 and a distal region 14 with a main body 16 extending therebetween. The deployable segment 8 includes a loop member 18 that spans generally from the proximal region 12 to the distal region 14 of the deployable segment 8. In the exemplary deployable segment 8 of FIG. 7, a compressive member 54 may be used to facilitate tightening of the loop member 18. The compressive member 54 may also be referred to as a stopper or cinching member. Various configurations of a compressive member 54 may be suitable, for example, a sleeve or a spring. U.S. Pat. No. 10,085,763 discloses additional embodiments of compressive members 54 and is herein incorporated by reference in its entirety.

The loop member 18 may be made of various suitable materials, with or without a coating. For example, the loop member 18 may include nylon monofilament. Alternatively, the loop member 18 may be made of a non-conductive material, such as polypropylene or another plastic. The loop member 18 may also include a wound cable, coated cable, or braided fibers. The loop member 18 may include a single material or multiple materials. In embodiments where the outer surface of the loop member 18 has an increased resistance to slip, such as a woven material, the slip resistance provides increased control during contact with patient tissue. In addition to being formed of a solid cord, the loop member 18 may be a hollow tube or spring, covered or uncovered.

In some embodiments, the loop member 18 includes a stretchy material, for example and without limitation, elastic, silicone, latex, neoprene, or other materials. A loop member 18 with stretchy properties may be used to provide a compressive effect to target tissue after placement of a deployable segment 8 within a patient.

Referring back to FIG. 1, the delivery segment 10 comprises a frame 20, which is operatively coupled to the loop member 18 of the deployable segment 8 in a delivery state. In one embodiment, the frame 20 of the delivery segment 10 comprises a generally circular or loop-shaped region at its distal end in an expanded state.

The frame 20 may additionally include a steering portion that extends proximally from the loop-shaped portion of the frame 20, and this steering portion may be integral or otherwise connected to the loop-shaped portion of the frame 20. The steering portion is engageable by a physician to help orient the frame 20 during positioning and/or deployment of the loop member 18 relative to tissue, as explained further below.

The loop-shaped portion of the frame 20 may comprise a shape-memory material, such as nitinol, or another suitable material capable of deploying to a predetermined shape. Such material of the frame 20 may allow the frame 20 to deflect or bend temporarily during use without bending permanently. The frame 20 wire may comprise a flat wire or a round wire, and in some embodiments may include multiple adjacent or overlapping wires forming the frame 20.

In some embodiments, the diameter of the frame 20 may be approximately equal to the gauge diameter of the loop member 18, when the loop member 18 is held in an open state by the frame 20, as explained further below. In some instances, such as depicted in FIG. 1, the loop member 18 may appear to comprise a slightly smaller or larger gauge diameter at certain locations around its perimeter in the open state, relative to the diameter of the frame 20. As will be appreciated, such actual or relative dimensions are not intended to be limiting, and it will be appreciated that a wide range of diameters may be selected, e.g., based on a particular application for the system 2, including but not limited to the size of tissue to be treated or engaged by the loop member 18 that is coupled to the frame 20.

Referring still to FIG. 1, the system 2 may further include a cannula 30 comprising a cannula lumen 32 extending therethrough. The cannula 30 is dimensioned to circumferentially surround at least a portion of the deployable segment 8 and at least a portion of the frame 20. In some embodiments, the outer surface of the cannula 30 may be sized such that the cannula 30 may pass through a channel of an endoscope (not shown). The cannula 30 may comprise a generally compression-resistant material, such as a single extruded material or may be formed using multiple materials. Exemplary, non-limiting materials may include nylon, Pebax®, or another thermoplastic. The cannula 30 may also include a reinforcing coil, braid, and/or liner.

In some embodiments, the cannula 30 is more flexible at a distal portion 33 of the cannula 30 than at a proximal portion 31 of the cannula. In some embodiments, 10% to 40% of the cannula is made of or comprises a more flexible material and 60% to 90% of the cannula is made of or comprises a stiffer material. Increased flexibility of the cannula 30 at the distal end 33 facilitates bending of the cannula 30 within an endoscope which may increase ease and predictability of movement of the cannula 30 during insertion and retraction.

In some embodiments, the distal region of the frame 20 is collapsible. The cannula 30 may be slid distally, along arrow 37, over the frame 20, for example during insertion or retraction of the system 2, thereby collapsing the frame 20. Distal sliding, along arrow 37, of the cannula 30 also collapses the loop member 18. Proximal sliding, along arrow 35, of the cannula 30, thereby exposing the frame 20 and/or loop member 18, may allow the frame 20 and loop member 18 to return to a predefined or predisposed shape.

Figure 3:
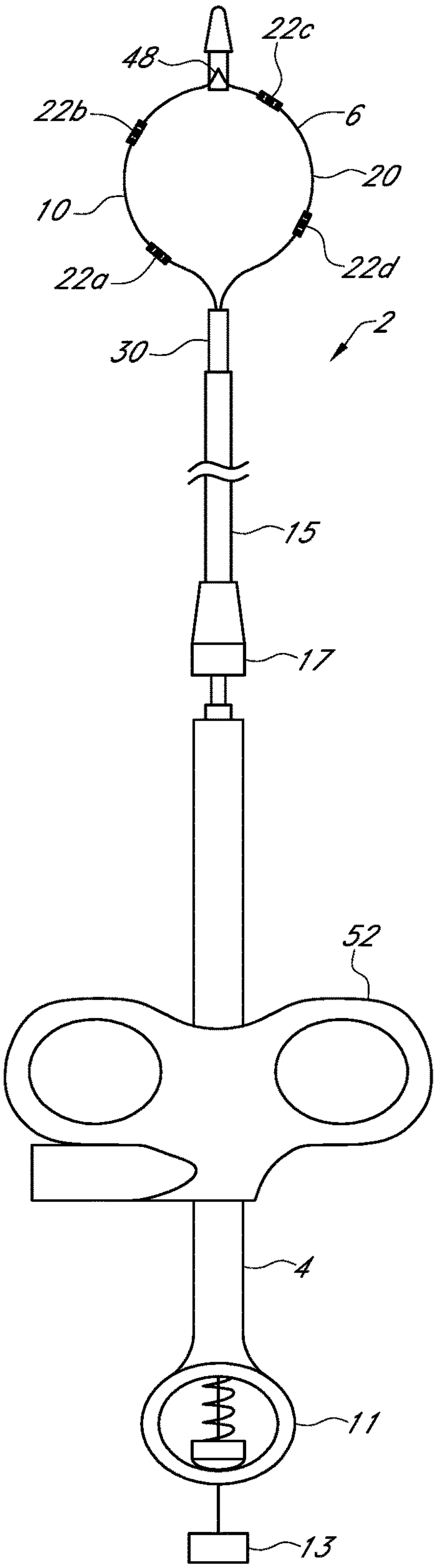
FIG. 3 is a front view of an embodiment of an apparatus including a frame at the distal end and a handle at the proximal end.
Figure 6:
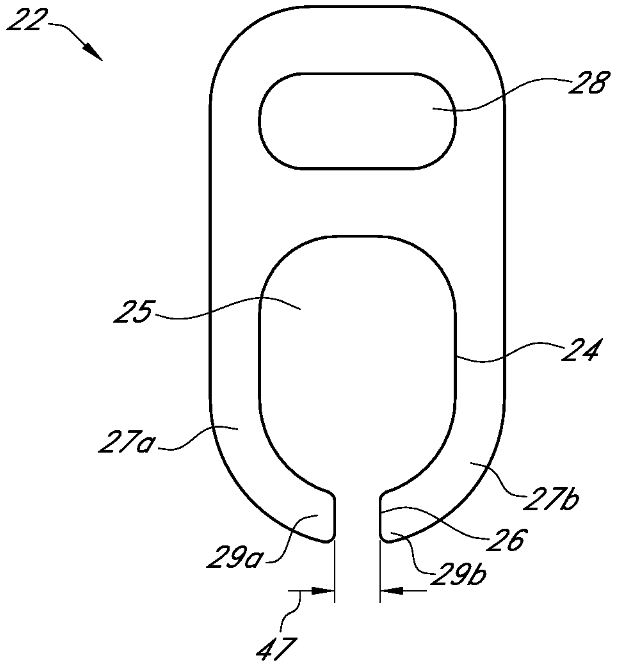
FIG. 6 is a cross-sectional view of an embodiment of a lug.

In some embodiments, as best seen in FIG. 1 and FIG. 3, the frame 20 is operatively coupled to the loop member 18 by at least one lug 22. One exemplary lug 22 is depicted in FIG. 6 in an isolated manner from a cross-sectional view. In the example of FIG. 6, the lug 22 defines a slit 24 having a first region 25 and a second region 26, where the first region 25 comprises a wider opening than the second region 26 in a relaxed state, as shown in FIG. 6.

In such embodiments, the lug 22 may be formed with first side 27*a* and second side 27*b* that bound the slit 24. The first and second sides 27*a* and 27*b* may taper inward at ends 29*a* and 29*b*, respectively, as shown in FIG. 6. Due to the ends being tapered inward, the second region 26 comprises a smaller opening width 47 than the first region 25. During delivery, the loop member 18 extends through the lug slit 24 and is held generally within the first region 25, which provides increased control of the loop member 18 circumference during use, as explained further below.

In some embodiments, the loop member 18 is snappable into the slit 24 of the lug 22, where it will be held during the delivery and pre-deployment state. The loop member 18 comprises a gauge diameter 48, and the opening at the second region 26 of the slit 24 is narrower than the loop member 18 gauge diameter 48. The loop member 18 is retained with the slit 24 such that the loop member 18 cannot pass through the slit opening 26 when external forces are not significantly applied to the loop member 18. More specifically, in the absence of significant external forces, the inherent properties of the first and second sides 27*a* and 27*b* of the lug 22, coupled with the size of the opening 26, are sufficient to retain the loop member 18 within the first region 25 of the lug 22 before desired deployment. However, the loop member 18 may be released from the lug 22 when an external force is applied that is sufficient to overcome the counteractive forces applied by the first and second sides 27*a* and 27*b* of the lug 22. Either the frame 20 and lug 22 may be held steady while the loop member 18 is moved, or vice versa, thereby causing the loop member 18 to move relative to the frame 20 and the lug 22, causing disengagement of the loop member 18 from the lug 22 upon such external force. For example, once the loop member 18 is cinched and secured to the target, the frame 20 is pulled away to decouple the loop member 18 from the lugs 22. In many instances, the act of cinching will release one (or more) lugs 22 as the loop member 18 is reduced.

In one embodiment, the frame 20 may be stiffer than the loop member 18, either due to material properties and/or increased thickness of materials associated with the frame 20. In this manner, the frame 20 may be more inclined to hold its shape when any external forces are applied that cause the loop member 18 to be reduced and detached from the lug 22.

The lug 22 comprises a suitable material, by way of example and without limitation, such as polycarbonate, and may be externally secured to the frame 20 or integrally formed with the frame 20. In the example depicted in FIG. 6, the lug 22 comprises a lug aperture 28, and the frame 20 extends through the aperture 28, wherein it may be secured by friction, an adhesive, solder, weld or any other known method in the art. Alternatively, the aperture 28 may be omitted, and the frame 20 may be secured to an exterior surface of the lug 22.

In one embodiment, the system 2 includes at least three lugs 22*a*, 22*b*, 22*c*. Each lug 22*a*, 22*b*, 22*c* may comprise a slit 24, such as the slit 24 explained with respect to FIG. 6 above. The loop member 18 extends through each lug slit 24 in the pre-deployment state and is therefore secured to the frame 20 as depicted in FIG. 1 and FIG. 3.

In one embodiment, the at least three lugs 22*a*, 22*b*, 22*c* are spaced apart substantially circumferentially along the frame 20 so that the first lug 22*a* is at least 15 degrees from the second lug 22*b*, and the second lug 22*b* is at least 15 degrees from the third lug 22*c*, thereby allowing a sufficient gap in-between selective lugs 22 to allow only periodic coupling of the loop member 18 to the frame 20. Advantageously, the selectively spaced-apart coupling locations may facilitate release of the loop member 18 from the frame 20 when an external force is applied, as opposed to a single elongated lug 22 which may require a higher force to release the loop member 18.

In other embodiments, the spacing in-between adjacent lugs 22 may be higher, such as about 30 degrees to about 90 degrees, greater than about 30 degrees, greater than about 45 degrees, greater than about 60 degrees, greater than about 75 degrees, greater than about 90 degrees, or more. Variation in the spacing may be tailored to a specifically desired release force for the loop member 18, e.g., more closely spaced lugs 22 may require a higher withdrawal force, whereas further spaced apart lugs 22 may require a lesser force applied.

In other embodiments, a fourth lug 22*d* may be provided, wherein each lug 22 is spaced apart from each of the other lugs 22. In this example, the at least four lugs 22*a*, 22*b*, 22*c*, 22*d* may be spaced apart substantially circumferentially along the frame 20 so that the first lug 22*a* is about 90 degrees from the second lug 22*b*, the second lug 22*b* is about 90 degrees from the third lug 22*c*, and the third lug 22*c* is about 90 degrees from the fourth lug 22*d*. However, as noted above, other lug 22 spacings may be used depending on the withdrawal force desired to release the loop member 18 from the frame 20.

In other embodiments, the frame 20 may be formed as one extrusion of the lug 22 cross-section, with or without the aperture 28. In this way, the loop member 18 is secured within the first region 25 and when under the proper withdrawal force, deployed via the formed outlet of the second region 26. These embodiments incorporate the functionality of the previously described lugs 22 within the structure of the frame 20, eliminating the need for lugs 22. In some embodiments, in which the aperture 28 is included in the extruded cross-section; wires, cords, cables and/or braided line can be inserted to incorporate desired mechanical properties. These mechanical properties may include but are not limited to; increased tension capabilities and/or shape memory capabilities.

Figure 5:
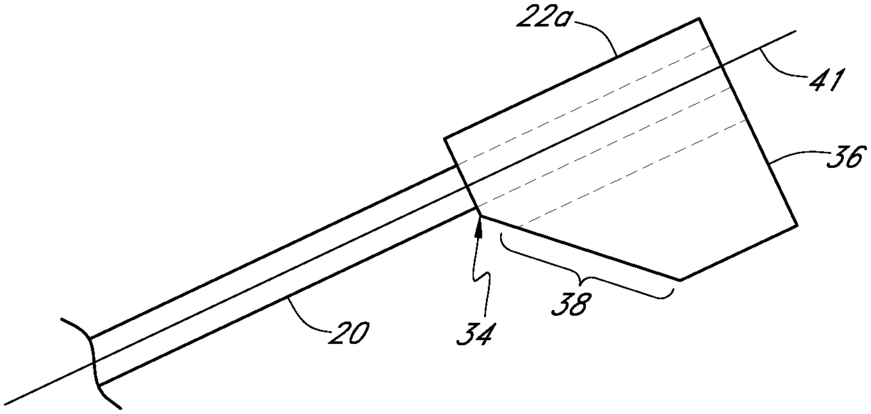
FIG. 5 is a side view of an embodiment of a segment of a frame with a lug.

Referring to FIG. 5, in some embodiments, one or more of the lugs 22 may comprise a first end 34 and a second end 36, with a taper 38 disposed at the first end 34. In embodiments with tapered lugs 22, the taper 38 may contribute to ease of re-sheathing the frame 20 with the cannula 30. The taper 38 may assist the cannula 30 in sliding by or along a lug 22, rather than abutting a portion of the lug 22 and requiring retraction for dislodging from the lug 22 before further re-sheathing of the frame 20 with the cannula 30.

Figure 2:
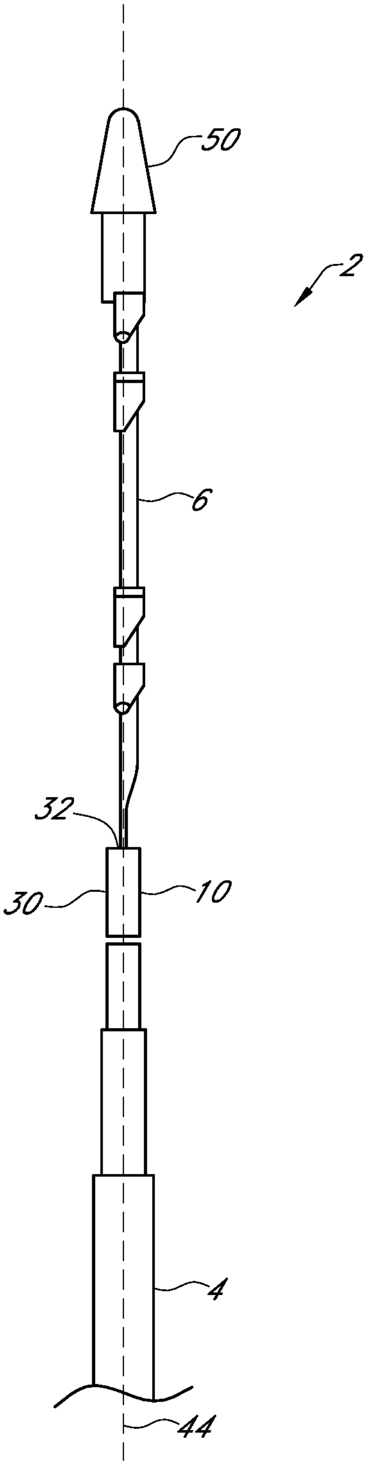
FIG. 2 is a side view of the apparatus of FIG. 1.

The frame 20 may be inclined to assume a state that is either on the same plane as the cannula 30 or angled relative to the cannula 30. In the example of FIGS. 1-3, the frame 20 is generally on the same plane as a cannula 30 longitudinal axis 41, which is the axis running through the cannula lumen 32, as shown in FIG. 5.

Figure 4:
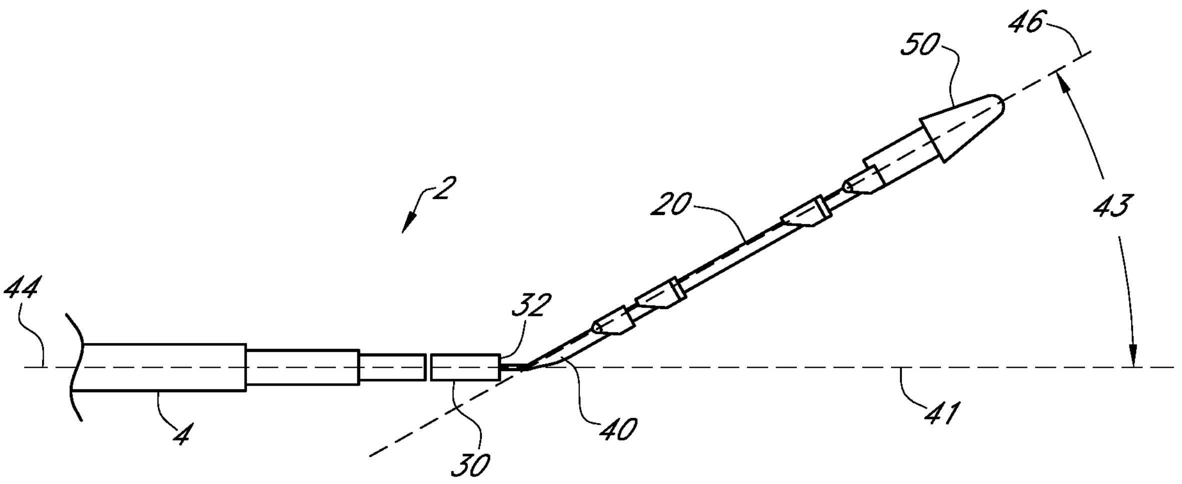
FIG. 4 is a side view of an embodiment of an apparatus including a frame and a loop member.

Alternatively, as shown in FIG. 4, the frame 20 may be angled out of and away from the cannula 30 longitudinal axis 41. In this embodiment, the frame 20 includes a bend 40 relative to a first longitudinal axis 41 of the proximal region 12 of the deployable segment 8. This bend 40 sets the frame 20 on a second longitudinal axis 46 at an intersecting angle equal to the bend 40 angle 43. The frame bend 40 is at an angle 43 within a range of about 0 degrees to about 90 degrees. For example, the frame bend 40 is angled at angle 43 between about 30 and 60 degrees, and in some embodiments between 40 and 45 degrees. The frame bend 40 is disposed proximal to the lugs 22 of the frame 20.

The frame bend 40 depicted in FIG. 4 may be achieved due to the properties of the frame 20, e.g., being made from a shape-memory material and designed to assume the bent state when released from the cannula 30 or when other forces are absent. Advantageously, the pre-disposed bend in the frame 20 may facilitate application of the loop member 18 around tissue, e.g., by providing a desirable leverage or angle during manipulation by a physician.

In some embodiments, such as shown in FIG. 1, at least a portion of the frame 20 may comprise a fold 48 at the distal region of the frame 20. The fold 48 may be at the distal apex of the frame 20. In some embodiments, the fold 48 contributes to orientation of the frame 20, and may also assist with collapse of the loop member 18 and frame 20, for example, during insertion or retraction of the system 2. In some embodiments, fold 48 may be generally v-shaped or u-shaped but could be any shape that facilitates bending or collapse.

A tip 50 may be coupled to the distal region of the frame 20. The tip 50 may be an atraumatic nose cone, and optionally, there may be a taper 38 at the distal end of the tip 50. The tip 50 may be attached to the frame 20 or integrally formed. For example, the tip 50 may be attached to the frame 20 using an adhesive. In some embodiments, the tip 50 includes a groove that contributes to attachment of the tip 50 to the frame 20. The tip 50 may also include a recess for the loop member 18, so that the recess provides clearance to accept at least a portion of the loop member 18 when the loop member 18 is collapsed and/or within a cannula 30. A diameter of the tip 50, or a diameter of a portion of the tip 50, may be less than the inner diameter of a cannula lumen 32.

In one exemplary method, the system 2 may be delivered to a target site within a patient's anatomy while the frame 20 and the loop member 18 are held in a delivery state within the cannula 30, more specifically, in the distal portion 33. The tip 50 facilitates atraumatic placement of the system 2 at a target site. As noted above, in some embodiments, the system 2 may be delivered via an endoscope, where the cannula 30 extends through a working channel of the endoscope.

The method further includes expanding the frame 20. Expanding the frame 20 may include extending the frame 20 from the cannula 30 in a distal direction 37 or retracting the cannula 30 in a proximal direction 35, thereby exposing the frame 20 and allowing it to assume its predefined shape, e.g., as shown in FIG. 1. If the frame 20 comprises a bend 40, e.g., as shown in FIG. 4, then the bend 40 may be attained when the frame 20 is released from the cannula 30 due to the material properties of the frame 20, as discussed above.

At this time, the loop member 18 is held in an open state since the loop member 18 is coupled to the one or more lugs 22 of the frame 20. As noted above, advantageously, the frame 20 contributes to the practitioner's ability to control insertion, placement, and deployment of the loop member 18. Further, the predefined bend 40 of the frame 20 may facilitate orientation of the loop member 18 relative to tissue. At this stage, a physician may place the loop member 18 over tissue, or otherwise engage or treat the tissue.

In embodiments in which the deployable segment 8 is detachable from the delivery segment 10, the practitioner may deploy the deployable segment 8 within the patient and remove the remainder of the system 2 from the patient. For example, segment 8 may be coupled to delivery system 10 by a flexible member that runs from an actuator in the handle and terminates with a distal hook or loop. This method may include retracting the loop member 18, wherein retracting the loop member 18 involves decoupling the loop member 18 from the one or more lugs 22 of the frame 20. In some embodiments, such as shown in FIG. 3, a practitioner may use an applicator handle 52. The applicator handle 52 may be connected to the proximal end of the frame 20. For example, the user applies force (e.g., pulls or pushes) on finger loops 52 relative to palm loop 11 to retract the hook and thereby reduce the loop member 18.

Handle 52 is coupled to the distal frame and loop assembly via a shaft composed of a few members (i.e., "nested" tubes & an inner control wire with distal hook). After cinching the loop, the hook is extended to expose the proximal end of the loop 12 from the inner lumen, which will free it from the confines of the lumen and allow it to be pulled free from the hook.

In some embodiments, loading button 13 is depressed to extend the hook for loading the loop onto the hook. And outer sheath hub 17 is used to retract outer sheath 15 to expose the loop assembly.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used in the description and claims, the singular form "a", "an" and "the" include both singular and plural references unless the context clearly dictates otherwise. For example, the term "lug" may include, and is contemplated to include, a plurality of lugs. At times, the claims and disclosure may include terms such as "a plurality," "one or more," or "at least one;" however, the absence of such terms is not intended to mean, and should not be interpreted to mean, that a plurality is not conceived.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

We claim:

1. An apparatus for treating tissue by applying a force to the tissue, the apparatus comprising:

a frame comprising a loop-shaped portion at its distal end;

a deployable segment having a proximal region and a distal region, and a main body extending therebetween, wherein the deployable segment comprises a loop member formed at the distal region of the deployable segment; and at least three lugs;

wherein the loop-shaped portion is operatively coupled to the loop member by the lugs; and wherein each lug defines a slit, and wherein the loop member extends through the slit of each lug wherein the loop member is held within the slits when external forces are not applied to the loop member; and when an external force is applied that is sufficient to overcome counteractive force applied by the lugs, the loop member will be released from the lugs with the lugs remaining coupled to the loop-shaped portion, thereby achieving a detachment of the loop member from the frame, such that the deployable segment is placed within a patient's body, maintaining engagement with tissue to provide a continuous compressive force upon the tissue, wherein the frame is stiffer than the loop member, and is inclined to hold its shape when external forces are applied to cause the loop member to be detached from the lug.

2. The apparatus of claim 1, wherein the at least three lugs each define a lug aperture, and wherein the frame is configured to extend through each lug aperture.

3. The apparatus of claim 1, wherein the at least three lugs comprise a first lug, a second lug, and a third lug, wherein the first lug is spaced apart from the second lug and the second lug is spaced apart from the third lug.

4. The apparatus of claim 1, wherein the loop member has a diameter, and the slit defines an opening having a width, wherein the width of the slit opening is less than the diameter of the loop member.

5. The apparatus of claim 1, wherein the at least three lugs comprise a first lug, a second lug, a third lug, and a fourth lug, wherein each lug is spaced apart from each of the other lugs.

6. The apparatus of claim 5, wherein the at least three lugs are spaced apart along the frame so that the first lug is about 60 degrees to about 100 degrees from the second lug, the second lug is about 60 degrees to 100 degrees from the third lug, and the third lug is about 60 degrees to about 100 degrees from the fourth lug.

7. The apparatus of claim 1, wherein each of the at least three lugs further comprises a first end and a second end, wherein one or more of the at least three lugs comprises a taper at the first end.

8. The apparatus of claim 1, further comprising a cannula comprising a lumen extending therethrough, wherein the cannula is dimensioned to circumferentially surround at least a portion of the deployable segment and at least a portion of the frame.

9. An apparatus for treating tissue by applying a force to the tissue, the apparatus comprising:

a frame comprising a loop-shaped portion at its distal end;

a deployable segment having a proximal region and a distal region, and a main body extending therebetween, wherein the deployable segment comprises a loop member formed at the distal region of the deployable segment;

wherein the loop-shaped portion operatively coupled to the loop member; and wherein the loop-shaped portion comprises coupling features configured for operatively coupling the loop member to the loop-shaped portion;

wherein the loop member is held within the coupling features when external forces are not applied to the loop member; and when an external force is applied that is sufficient to overcome counteractive force applied by the coupling features, the loop member will be released from the coupling features with the coupling features remaining coupled to the loop-shaped portion, thereby achieving the detachment of the loop member from the frame, such that the deployable segment is placed within a patient's body, maintaining engagement with tissue to provide a continuous compressive force upon the tissue, wherein the frame is stiffer than the loop member, and is inclined to hold its shape when external forces are applied to cause the loop member to be detached from the coupling features.

10. The apparatus of claim 9, wherein the coupling features comprise at least three lugs, wherein each lug defines a slit, and wherein the loop member extends through each lug slit.

11. The apparatus of claim 10, wherein the at least three lugs each further define a lug aperture, and wherein the frame is configured to extend through each lug aperture.

12. The apparatus of claim 10, wherein the at least three lugs comprise a first lug, a second lug, and a third lug, wherein the first lug is spaced apart from the second lug and the second lug is spaced apart from the third lug.

13. The apparatus of claim 10, wherein the loop member has a diameter, and the slit defines an opening having a width, wherein the width of the slit opening is less than the diameter of the loop member.

14. The apparatus of claim 10, wherein the at least three lugs further comprise a first lug, a second lug, a third lug, and a fourth lug, wherein each lug is spaced apart from each of the other lugs.

15. The apparatus of claim 14, wherein the at least three lugs are spaced apart along the frame so that the first lug is about 60 degrees to about 100 degrees from the second lug, the second lug is about 60 degrees to about 100 degrees from the third lug, and the third lug is about 60 degrees to about 100 degrees from the fourth lug.

16. The apparatus of claim 10, wherein each of the at least three lugs further comprises a first end and a second end, wherein one or more of the at least three lugs comprise a taper at the first end.

17. The apparatus of claim 9, further comprising a cannula comprising a lumen extending therethrough, wherein the cannula is dimensioned to circumferentially surround at least a portion of the deployable segment and at least a portion of the frame.

18. The apparatus of claim 17, wherein the cannula comprises:

i. a distal portion, ii. a proximal portion, and b. wherein the distal portion is more flexible than the proximal portion.

19. The apparatus of claim 18, wherein the distal portion comprises about 10% to about 40% of the cannula and the proximal portion comprises about 60% to about 90% of the cannula.

20. An apparatus for treating tissue by applying a force to the tissue, the apparatus comprising:

a frame comprising a loop-shaped portion at its distal end;

a deployable segment having a proximal region and a distal region, and a main body extending therebetween, wherein the deployable segment comprises a loop member formed at the distal region of the deployable segment; and wherein the loop-shaped portion is operatively coupled to the loop member, wherein the loop member remains being coupled to the loop-shaped portion when external forces are not applied; and when an external force sufficient to overcome a counteractive applied by the annular portion is applied, the loop member will be released from the loop-shaped portion, thereby achieving a detachment of the loop member from the frame, such that the deployable segment is placed within a patient's body, maintaining engagement with tissue to provide a continuous compressive force upon the tissue, wherein the frame is stiffer than the loop member, and is inclined to hold its shape when external forces are applied to cause the loop member to be detached from the loop-shaped portion, wherein the frame comprises a proximal region and a distal region, wherein the frame assumes a plane that is angled relative to a first longitudinal axis of the proximal region of the deployable segment.

21. The apparatus of claim 20, further comprising at least two lugs configured to couple the frame to the loop member.

22. The apparatus of claim 21, wherein the plane assumed by the frame intersects with the first longitudinal axis of the proximal region of the deployable segment at a position proximal to the at least two lugs.

23. The apparatus of claim 20, wherein the distal region of the frame is collapsible and wherein the frame comprises a loop shape.

24. The apparatus of claim 20, wherein an angle between the plane assumed by the frame relative to the first longitudinal axis of the proximal region of the deployable segment is within a range of about 0 degrees to about 90 degrees.

25. The apparatus of claim 20, wherein at least a portion of the frame comprises a fold at the distal region of the frame.

26. The apparatus of claim 20, further comprising a tip coupled to the distal region of the frame.

27. The apparatus of claim 20, further comprising a cannula comprising a lumen extending therethrough, wherein the cannula is dimensioned to circumferentially surround at least a portion of the deployable segment and at least a portion of the frame.

28. The apparatus of claim 27, wherein the frame comprises a second longitudinal axis, wherein the second longitudinal axis and the first longitudinal axis intersect.

29. The apparatus of claim 27, wherein the loop shape of the frame is disposed within the distal portion of the cannula.

30. The apparatus of claim 27, wherein the cannula comprises:

i. a distal portion, ii. a proximal portion, and b. wherein the distal portion is more flexible than the proximal portion.

31. The apparatus of claim 30, wherein the distal portion comprises about 10% to about 40% of the cannula and the proximal portion comprises about 60% to about 90% of the cannula.

32. A method of treating tissue by applying a force to the tissue, the method comprising:

inserting an apparatus for treating tissue by applying a force to the tissue in a patient, wherein the apparatus comprises a frame comprising a loop-shaped portion at its distal end; and a deployable segment having a proximal region and a distal region, and a main body extending therebetween, wherein the deployable segment comprises a loop member formed at the distal region of the deployable segment;

wherein the loop-shaped portion is operatively coupled to the loop member;

expanding the loop-shaped portion;

retracting the loop member, wherein retracting the loop member comprises decoupling the loop member from the loop-shaped portion; and deploying the deployable segment, such that the deployable segment is placed within a patient's body, maintaining engagement with tissue to provide a continuous compressive force upon the tissue, wherein the frame is stiffer than the loop member, and is inclined to hold its shape when external forces are applied to cause the loop member to be detached from the loop-shaped portion.

33. The method of claim 32, wherein the frame is operatively coupled to the loop member by at least two lugs movably coupled to the frame.

34. The method of claim 32, wherein expanding the frame further comprises extending the frame from a cannula in a distal direction, wherein the frame further comprises a bend relative to a first longitudinal axis of the proximal region of the deployable segment.

35. The method of claim 34, wherein the bend is an angle within a range of about 0 degrees to about 90 degrees.

* * * * *